United States Patent
Ceccoli et al.

(10) Patent No.: US 10,301,248 B2
(45) Date of Patent: May 28, 2019

(54) COMPOSITIONS AND METHODS COMPRISING RESVERATROL

(71) Applicant: Biocogent, LLC, Stony Brook, NY (US)

(72) Inventors: Joseph D. Ceccoli, Farmingville, NY (US); Michael L. Ingrassia, Hauppauge, NY (US); Christopher M. Judd, Rivehead, NY (US); Brian R. Costello, Port Jefferson Station, NY (US)

(73) Assignee: Biocogent, LLC, Stony Brook, NY (US)

( * ) Notice: Subject to any disclaimer, the term of this patent is extended or adjusted under 35 U.S.C. 154(b) by 0 days.

(21) Appl. No.: 15/115,338

(22) PCT Filed: Feb. 5, 2015

(86) PCT No.: PCT/US2015/014629
§ 371 (c)(1),
(2) Date: Jul. 29, 2016

(87) PCT Pub. No.: WO2015/120153
PCT Pub. Date: Aug. 13, 2015

(65) Prior Publication Data
US 2017/0233326 A1    Aug. 17, 2017

Related U.S. Application Data

(60) Provisional application No. 62/054,553, filed on Sep. 24, 2014, provisional application No. 61/936,490, filed on Feb. 6, 2014.

(51) Int. Cl.
*C07C 67/08* (2006.01)
*A61K 8/37* (2006.01)
*A61K 31/618* (2006.01)
*A61Q 19/00* (2006.01)
*C07C 69/84* (2006.01)

(52) U.S. Cl.
CPC ............... *C07C 67/08* (2013.01); *A61K 8/37* (2013.01); *A61K 31/618* (2013.01); *A61Q 19/00* (2013.01); *C07C 69/84* (2013.01); *A61K 2800/10* (2013.01)

(58) Field of Classification Search
CPC ..................................................... C07C 67/08
See application file for complete search history.

(56) References Cited

U.S. PATENT DOCUMENTS

| | | | |
|---|---|---|---|
| 6,572,882 B1 | 6/2003 | Vercauteren et al. |
| 7,714,161 B2 | 5/2010 | Andrus et al. |
| 8,461,200 B2 | 6/2013 | Maes et al. |
| 8,575,217 B2 | 11/2013 | Mian et al. |
| 2009/0068132 A1 | 3/2009 | Bratescu et al. |
| 2012/0288460 A1 | 11/2012 | Maes et al. |
| 2013/0338120 A1 | 12/2013 | Sang |

FOREIGN PATENT DOCUMENTS

| | | |
|---|---|---|
| CN | 101854903 A | 10/2010 |
| CN | 102427809 A | 4/2012 |
| WO | 2004000302 A1 | 12/2003 |
| WO | 2006029484 | 3/2006 |

OTHER PUBLICATIONS

European Search Report dated Oct. 4, 2017.
International Search Report dated Apr. 15, 2015.

*Primary Examiner* — Shawquia Jackson
(74) *Attorney, Agent, or Firm* — Saul Ewing Arnstein & Lehr LLP; Domingos J. Silva

(57) ABSTRACT

The present technology relates to synthesis of resveratrol compositions, in particular to methods of synthesizing resveratrol salicylates such as those formed through the activation of resveratrol and salicylic acid, and cosmetic and pharmaceutical compositions comprising the same.

9 Claims, 26 Drawing Sheets

Example 2 Continued

- Precipitated Solid Product solubilized with Ethyl Acetate
- Solution containing product was mixed vigorously in water to remove impurities.
- Ethyl acetate solution containing product was collected using a separatory funnel.
- Solution containing product separated from solvent using a rotary evaporator under vacuum.
- Dry solids removed by from flask manually

FIG. 3

EXAMPLE 3

- Resveratrol + Salicylic acid

| Solvent

- Resveratrol and Salicylic Acid solution

| Activator

- Activated Resveratrol & Salicylic Acid (Highly exothermic process requires cooling)

- Maintain about 10 to about 85°C for about 24 hours

FIG. 4

Example 3 Continued
Purification and drying of final product

- Reaction Mixture is filtered to remove solids (such as dicyclohexylurea)
- Supernatant collected and dried using an evaporator/dryer to concentrate desired solids while maintaining solubility
- Small volume of water is added to neutralize any activated DCC
- Dry to solids (removal of solvent & $H_2O$) to yield final product

FIG. 5

Synthetic Approach
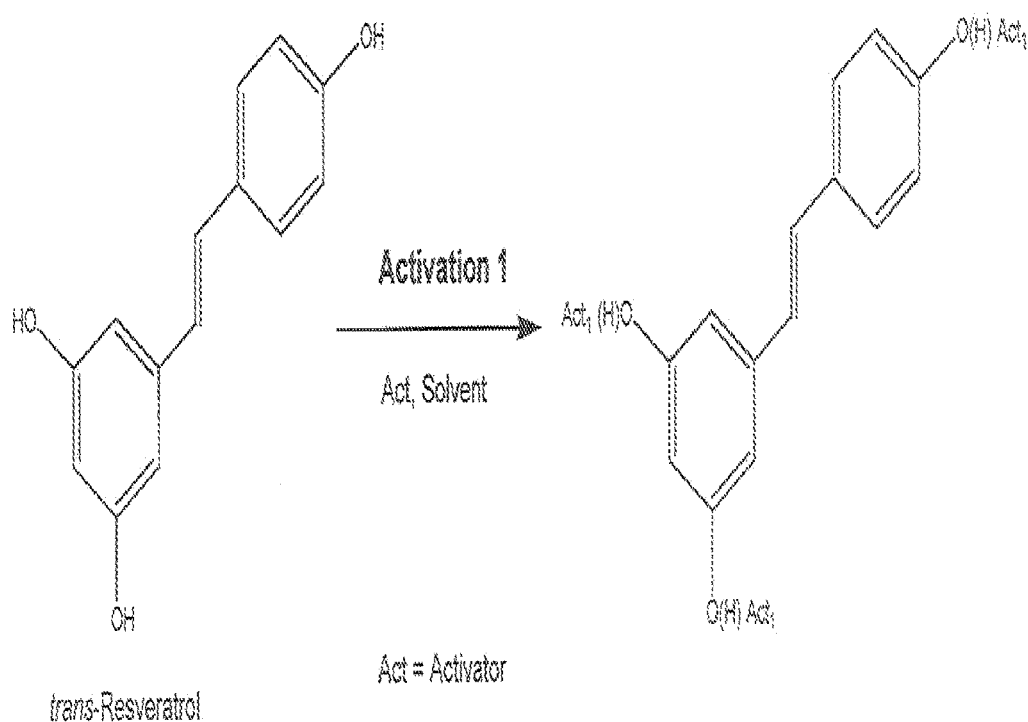
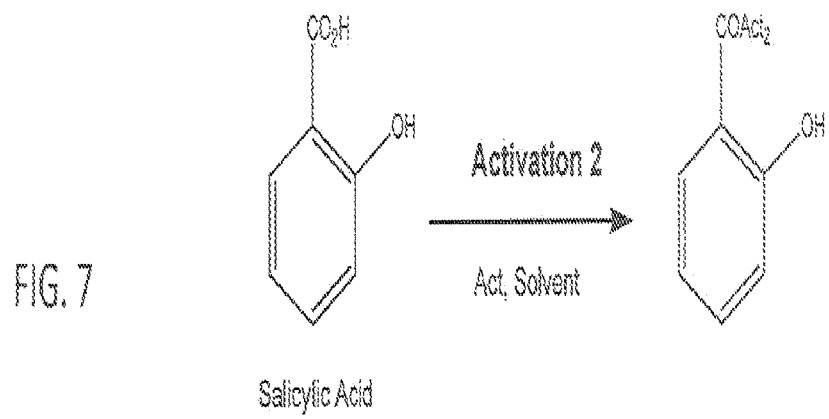
FIG. 7

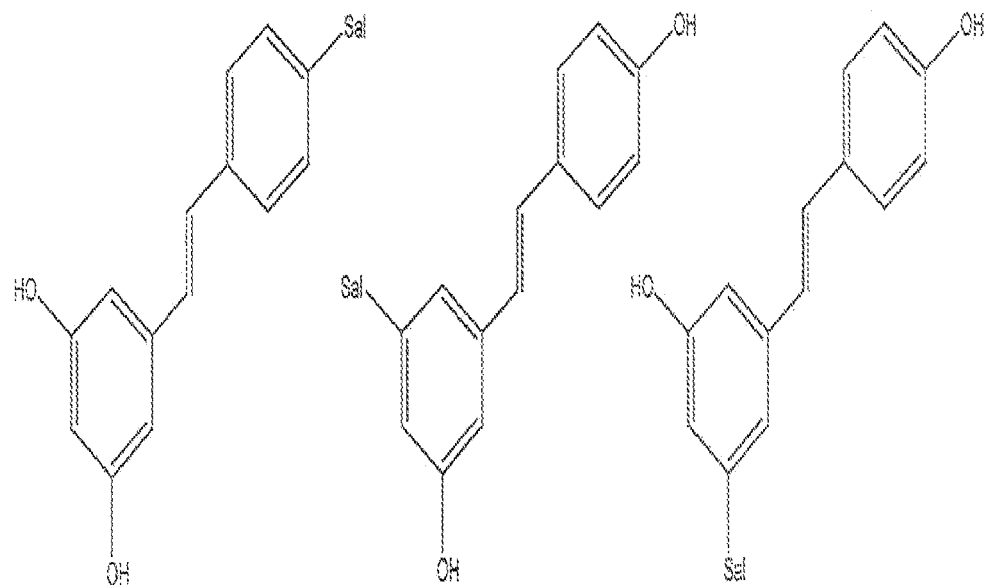
Monosubstituted Resveratrol Salicylates
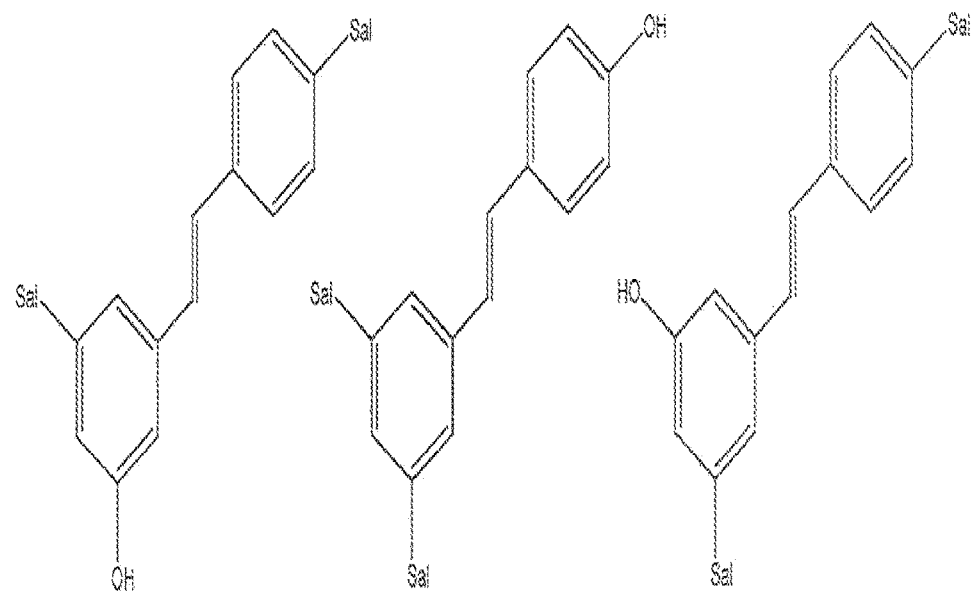
FIG. 10
Disubstituted Resveratrol Salicylates

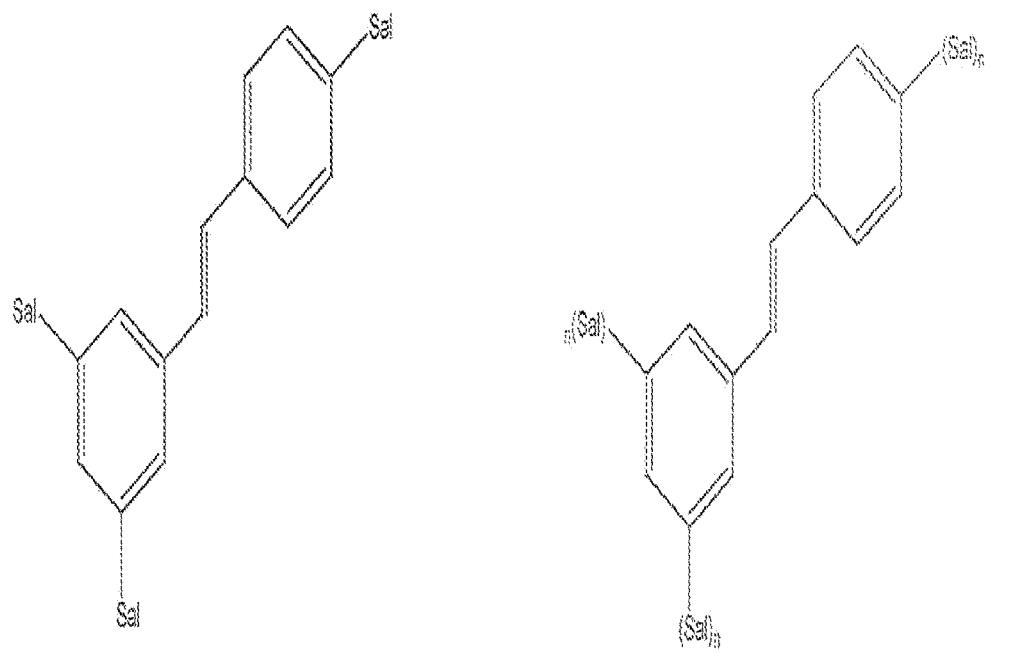
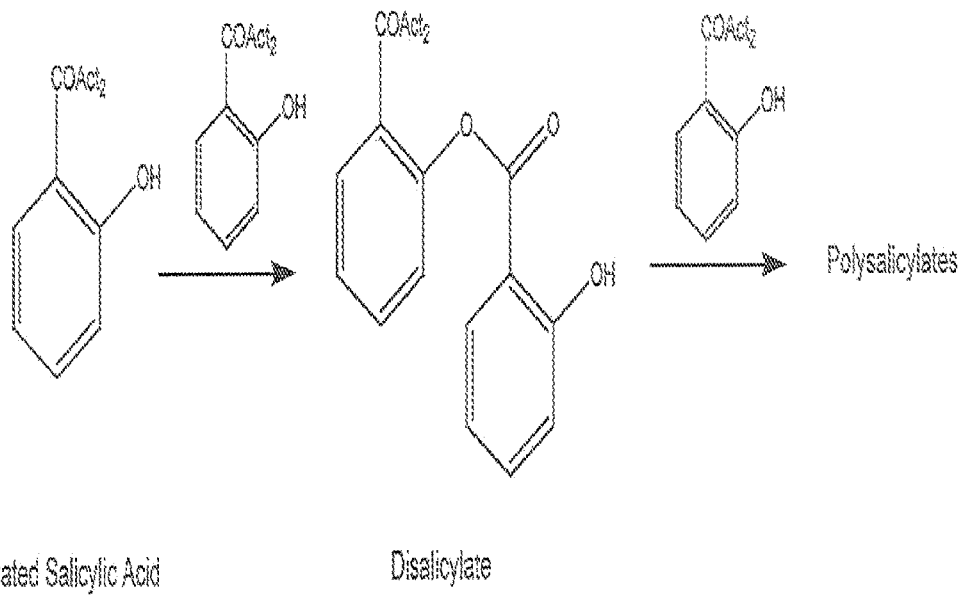
FIG. 11

FIG. 12 Top: Reaction Mixture 3rd: 11.1 min peak + 50-μMol NaOH
2nd: 11.1 min peak isolated    4th: 11.1 min peak +500-μMol NaOH Top: Reaction Mixture 3rd: 15.8 min peak + 50-μMol NaOH
2nd: 15.8 min peak isolated    4th: 15.8 min peak +500-μMol NaOH Top: Reaction Mixture 3rd: 19.1 min peak + 50-μMol NaOH
2nd: 19.1 min peak isolated    4th: 19.1 min peak +500-μMol NaOH FIG. 19   Negative Ion Mode [M-H], Main product, peak 15.8 min FIG. 20 HPLC Gradient FIG. 21  DPPH (2,2-diphenyl-1-picrylhydrazyl)

COMPOSITIONS AND METHODS COMPRISING RESVERATROL

CROSS-REFERENCE TO RELATED APPLICATIONS

This application is a U.S. national phase application filed under 35 U.S.C. § 371 claiming priority to International Patent Application No. PCT/US2015/014629, filed Feb. 5, 2015, which claims priority under 35 U.S.C. § 119(e) to U.S. Provisional Patent Application No. 61/936,490, filed Feb. 6, 2014, and U.S. Provisional Patent Application No. 62/054,553, filed Sep. 24, 2014, all of which applications are hereby incorporated herein by reference in their entireties.

BACKGROUND

The present technology relates to synthesis of resveratrol compositions, in particular resveratrol salicylates, and cosmetic and pharmaceutical compositions comprising the same.

Resveratrol (3,4',5-trihydroxy-trans-stilbene) is a polyphenol that occurs naturally in at least 72 plant species. It is a powerful antioxidant that is superior to vitamins C and E as well as propyl gallate. It is also present in nature in the cis form, and often occurs as the glycoside polydatin (piceid).

Attempts have been made to incorporate resveratrol and compounds comprising resveratrol into cosmetic and pharmaceutical compositions. However, its relative instability has continued to present challenges. Thus, a need exists for improved methods for synthesizing compounds containing resveratrol, as well as compositions comprising such compounds.

SUMMARY OF THE DISCLOSED TECHNOLOGY

In certain embodiments, the present technology is directed to a method of synthesizing a resveratrol salicylate, the method comprising the steps of: (a) activating resveratrol in the presence of a first solvent to produce activated resveratrol; (b) activating salicylic acid in the presence of a second solvent to produce activated salicylic acid; and (c) combining the activated resveratrol and the activated salicylic acid to produce a resveratrol salicylate mixture.

In certain embodiments, the present technology is directed to a method of synthesizing a mixture of mono-, di-, tri- or poly-substituted resveratrol salicylates, the method comprising the steps of: (a) combining activated salicylic acid with activated resveratrol in one or more solvents; and (b) controlling the ratio or percentage of di-, tri- or poly-substituted resveratrol by controlling the molar ratio of activated salicylic acid to activated resveratrol.

In certain embodiments, the present technology is directed to a mixture of resveratrol salicylates, the mixture comprising (a) mono-substituted resveratrol salicylates; and (b) di- and tri-substituted resveratrol salicylates. In certain embodiments, the mixture may comprise any two or more of the following: (a) mono-substituted resveratrol salicylates; (b) di-substituted resveratrol salicylates; (c) tri-substituted resveratrol salicylates; or (d) poly-substituted salicylates.

In certain embodiments, the present technology is directed to a method of synthesizing a mixture of mono-, di- or tri-substituted resveratrol salicylates, the method comprising the steps of:
(a) combining activated salicylic acid with activated resveratrol in one or more solvents; and
(b) controlling the ratio of di-, tri- or poly-substituted resveratrol salicylates by varying the molar ratio of activated salicylic acid to activated resveratrol.

In certain embodiments, the present technology is directed to a method of synthesizing a resveratrol salicylate, the method comprising the steps of:
(a) Combining resveratrol and salicylic acid with a solvent to provide a solution comprising resveratrol and salicylic acid; and
(b) contacting the solution with an activator to provide a solution comprising activated salicylic acid.

BRIEF DESCRIPTION OF THE FIGURES

FIGS. 1-6 show further details regarding various embodiments of the technology discussed herein, including Examples 2 and 3.

FIGS. 7-8 show further details and reaction steps relating to various embodiments of the technology discussed herein, including Example 1.

FIGS. 10-11 show reaction steps relating to the synthesis of mono-, di-, tri- and polysubstituted salicylates according to various embodiments herein.

DETAILED DESCRIPTION

Figure 1:
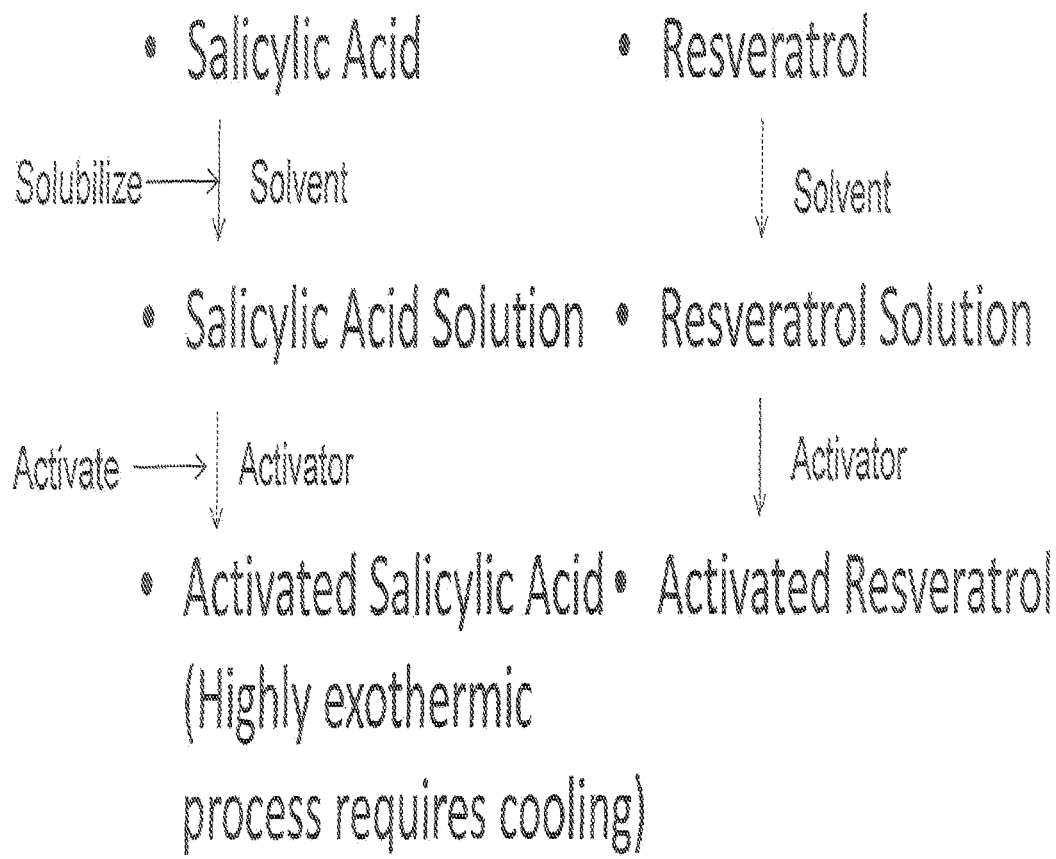

Resveratrol is highly unstable; it is labile in both strongly acidic and strongly basic conditions. It undergoes extensive oxidation in basic solutions. When irradiated with UV light having a wavelength in the range of 350 to 360 nm, trans-resveratrol photoisomerizes to its cis-isomer. Cis-resveratrol is less stable and biologically less active. The presence of multiple hydroxyl (—OH) functional groups on its basic stilbene structure predisposes resveratrol to a variety of chemical reactions such as aromatic electrophilic substitution.

It has been developed herein a new synthetic approach to converting resveratrol to a mixture of resveratrol salicylates. In certain embodiments, the methods herein produce not only monosubstituted resveratrol salicylate, but also di-substituted, tri-substituted and poly-substituted resveratrol salicylate, including forms that are mono-, di-, tri- and poly-substituted (that is, substituted with more than 3) with polysalicylate residues of varying size.

In certain embodiments, the methods comprise the following steps: (1) obtaining resveratrol, subjecting it to an activator and a solvent to produce activated resveratrol; (2) obtaining salicylic acid, subjecting it to an activator and a solvent to produce activated salicylate.

Examples of useful salicylic acid activators include, but are not limited to the following—

Carbodiimides, including but not limited to: N,N'-Dicyclohexylcarbodiimide (DCC); N,N'-diisopropylcarbodiimide (DIC); N-Cyclohexyl-N'-(2-morpholinoethyl) carbodiimide metho-p-toluenesulfonate (CMC); 1-tert-Butyl-3-ethylcarbodiimide; 1-Ethyl-3-(3-dimethylaminopropyl) carbodiimide (EDC); N,N'-Di-tert-butylcarbodiimide; N-(3-Dimethylaminopropyl)-N'-ethylcarbodiimide; or 1,3-Di-p-tolylcarbodiimide;

Diimidazoles, including but not limited to: 1,1'-Carbonyldiimidazole; 1,1'-Thiocarbonyldiimidazole; or 1,1'-Oxalyldiimidazole;

Uronium and Phosphonium reagents, including but not limited to: O-(Benzotriazol-1-yl)-N,N,N',N'-tetramethyluronium tetrafluoroborate; (7-Azabenzotriazol-1-yloxy) tripyrrolidinophosphonium hexafluorophosphate; (Benzotriazol-1-yloxy) tris(dimethylamino)phosphonium hexafluorophosphate; N,N,N',N'-Tetramethyl-O—(N-succinimidyl) uronium tetrafluoroborate (TSTU); 1-[Bis(dimethylamino)methylene]-1H-1,2,3-triazolo[4,5-b]pyridinium 3-oxid hexafluorophosphate (HATU); N,N,N',N'-Tetramethyl-O-(1H-benzotriazol-1-yl)uronium hexafluorophosphate (HBTU); or (1-Cyano-2-ethoxy-2-oxoethylidenaminooxy)dimethylaminomorpholinocarbenium hexafluorophosphate (COMU).

Examples of useful resveratrol activators include, but are not limited to the following—

1,8-Diazabicycloundec-7-ene (DBU); 1,5-Diazabicyclo[4.3.0]non-5-ene (DBN); Triethylamine (TEA); 2,6-Di-tert-butylpyridine; Phosphazene bases (t-Bu-P4, BEMP); Hünig's base (diisopropylethylamine, DIPEA); or 2,2,6,6-Tetramethylpiperidine (TMP).

Examples of useful solvents include, but are not limited to the following—

Polar aprotic solvents, e.g., acetonitrile; dimethylsulfoxide (DMSO); Hexamethylphosphoramide (HMPA); 1,3-Dimethyl-3,4,5,6-tetrahydro-2(1H)-pyrimidinone (DMPU); 1,3-Dimethyl-2-imidazolidinone (DMI); dimethylformamide (DMF); or 1-Methyl-2-pyrrolidinone (NMP) or dimethylaminopyridine (DMAP).

In certain embodiments, the activation can be carried out separately for resveratrol and salicylic acid. In one non-limiting example, resveratrol can be activated by treatment with a resveratrol activator in a solvent. Similarly, salicylic acid can be activated by treatment with a solvent using an excess a salicylic activator. In various embodiments, the coupling reaction may then be run in a 1.5:1 mixture (v/v) of the two solvents. In other examples, carbodiimides may be used for activation of salicylic acid, alone or in combination with other molecules such as N-hydroxysuccinimide (NHS).

Example 1

In a non-limiting example, the resveratrol activation is run for about 10 min at room temperature. As salicylic acid activation is an exothermic process, the reaction flask may be kept in a cooling bath while the salicylic acid activator is added in portions over a period of about 1 to about 15 minutes, depending on the reaction scale. In this example, the salicylic acid was activated with N,N'-diisopropylcarbodiimide (DIC) or dicyclohexylcarbodiimide (DCC). Upon completion of salicylic acid activator addition, the cooling bath may (but need not) be removed. This activation can also be run for about 30 to about 90 minutes, or more. The resveratrol can be activated with Hunig's Base. The reaction mixture containing activated resveratrol may then be combined with the activated salicylic acid. The resulting mix may be stirred at room temperature for, in various embodiments, up to about 72 hours, or about 1, about 2, or about 3 days.

As demonstrated herein, the resveratrol salicylates product distribution is dependent on the molar ratio of activated salicylic acid to activated resveratrol, with higher ratio favoring a more substituted product. Thus, in certain embodiments, the resveratrol salicylate mixture comprises mono-, di- and tri-substituted resveratrol salicylates; the ratios of the various substituted resveratrol salicylates in the mixture can be controlled by varying the molar ratio of activated salicylic acid to activated resveratrol, with higher ratios of the activated salicylic acid generally leading to more highly-substituted products. Thus in certain embodiments, the resveratrol salicylate mixture comprises mono-, di-, and tri-substituted resveratrol, and other polymeric salicylates on one or more hydroxyl groups of resveratrol—in other words, one or more salicylic acid molecules conjugated to any one or more/all hydroxyls on resveratrol.

Thus, in certain embodiments, an investigator can optimize or control the relative proportions of mono-, di-, tri- and polysalicylate-substituted resveratrol by varying or controlling the molar ratios of the activated salicylic acid and activated resveratrol. For example, the investigator may choose to increase the amount of mono-substituted resveratrol salicylates by decreasing the molar ratio of activated salicylic acid to activated resveratrol; conversely, if he wishes for a greater proportion of di-, tri- or polysalicylate-substituted resveratrol, he can optimize these amounts by increasing the molar ratio of activated salicylic acid to activated resveratrol. Indeed, in certain embodiments, the investigator may decide that maximizing the proportion of higher-substituted end product is a more beneficial way to engage the methods herein.

Example 2

Figure 2:
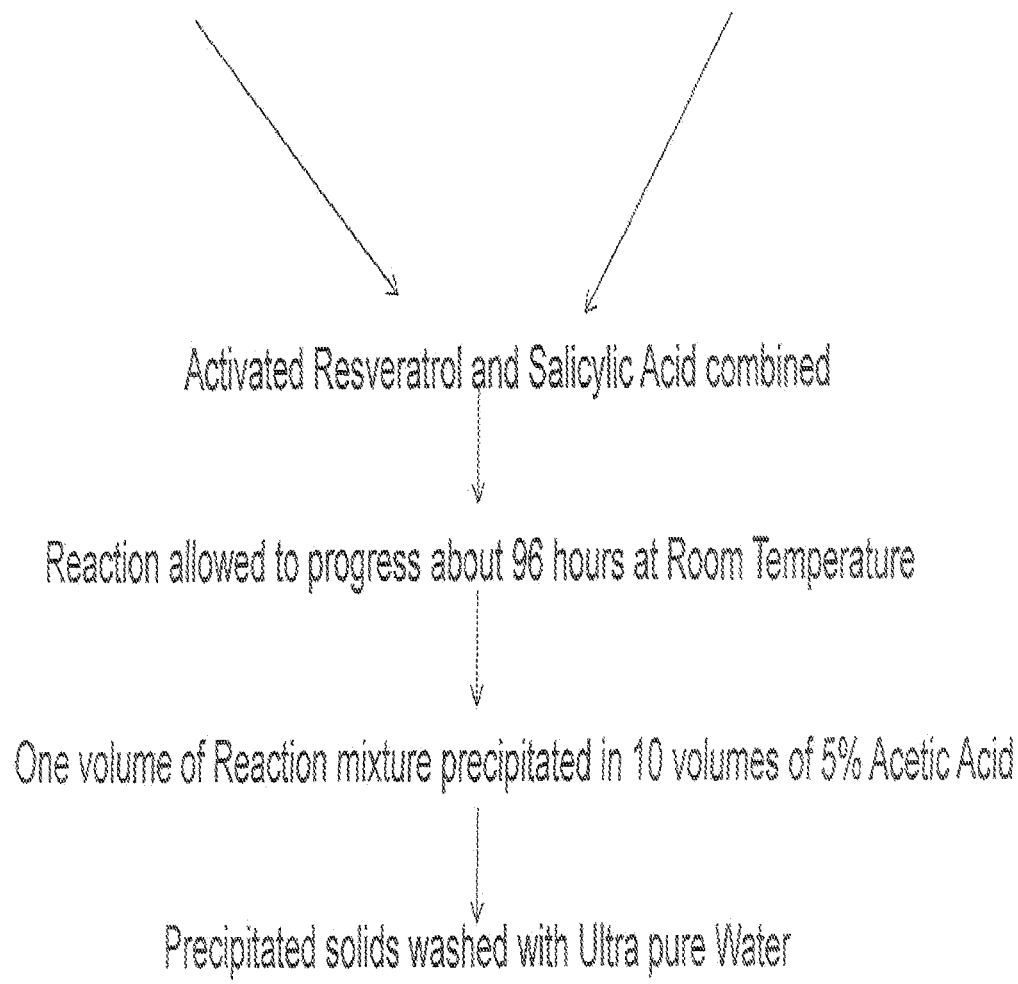

In another non-limiting example, the process for synthesizing resveratrol salicylates includes a two part, dual activation process. Salicylic acid is converted to a salicylic acid solution with addition of dimethyl formamide, and then activated with diisopropylcarbodiimide (DIC) to provide activated salicylic acid, a highly exothermic process the requires cooling. An exemplary schematic is shown in FIG. 1. Resveratrol is converted to a resveratrol solution with addition of dimethyl sulfoxide, and then activated with diisopropylethylamine to provide activated resveratrol. The activated resveratrol and activated salicylic acid are then combined, and the reaction is allowed to progress about 96 hours at room temperature. The precipitated solids are washed with ultra pure water, and solubilized with ethyl acetate; as shown, e.g., in FIG. 2. Further, the precipitated solid product was solubilized with ethyl acetate, to produce a solution that contained the product. The solution was mixed vigorously in water to remove impurities, then collected using a separatory funnel. The solvent was then separated with a rotary evaporator under vacuum, and the dry solids were manually removed from the flask, e.g., as shown in FIG. 3.

Example 3

In another non-limiting example, the following was observed: In certain embodiments, the present technology is directed to a single solvent, single activation reaction of salicylic acid, resveratrol and acetonitrile with DCC. An exemplary schematic is shown in FIG. 4. Such reaction differs from other embodiments of the technology that are directed to a two part, dual activation process that requires more clean-up and purification (e.g., Example 2). In this Example, resveratrol and salicylic acid are together in a solution with acetonitrile. The solution is activated with dicyclohexylcarbodiimide (DCC) via controlled addition to provide activated resveratrol and salicylic acid (a highly exothermic process that requires cooling). This solution is maintained at about 10 to about 85 degrees C. for about 24 hours, after which the reaction mixture is filtered to remove solids including dicyclohexylurea. The supernatant is collected and dried using an evaporator or dryer to concentrate the desired solids while maintaining solubility. A small volume of water may be added to neutralize any activated DCC, and the material is dried to yield the final product, e.g., as shown in FIG. 5.

Figure 6:
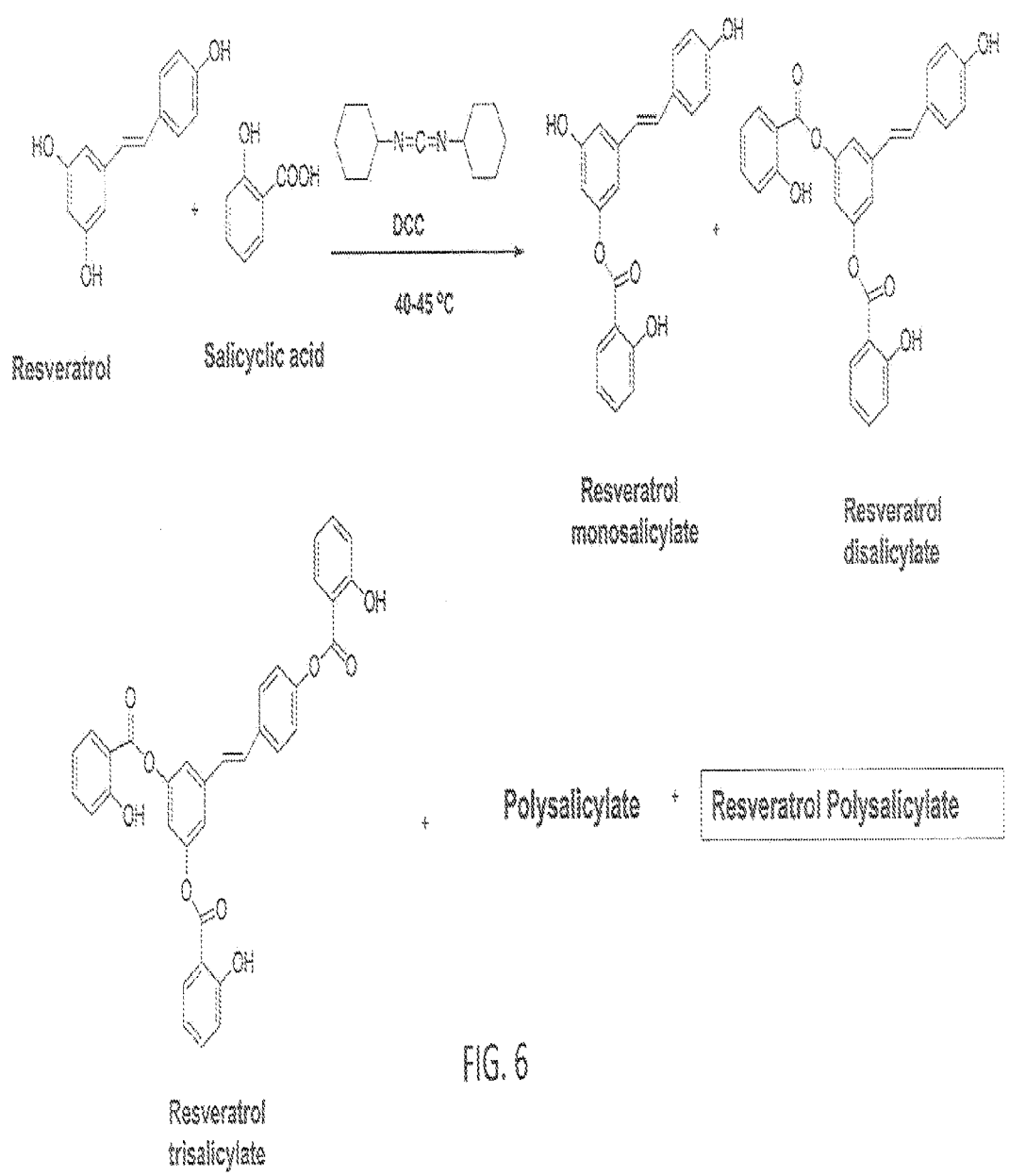
Figure 8:
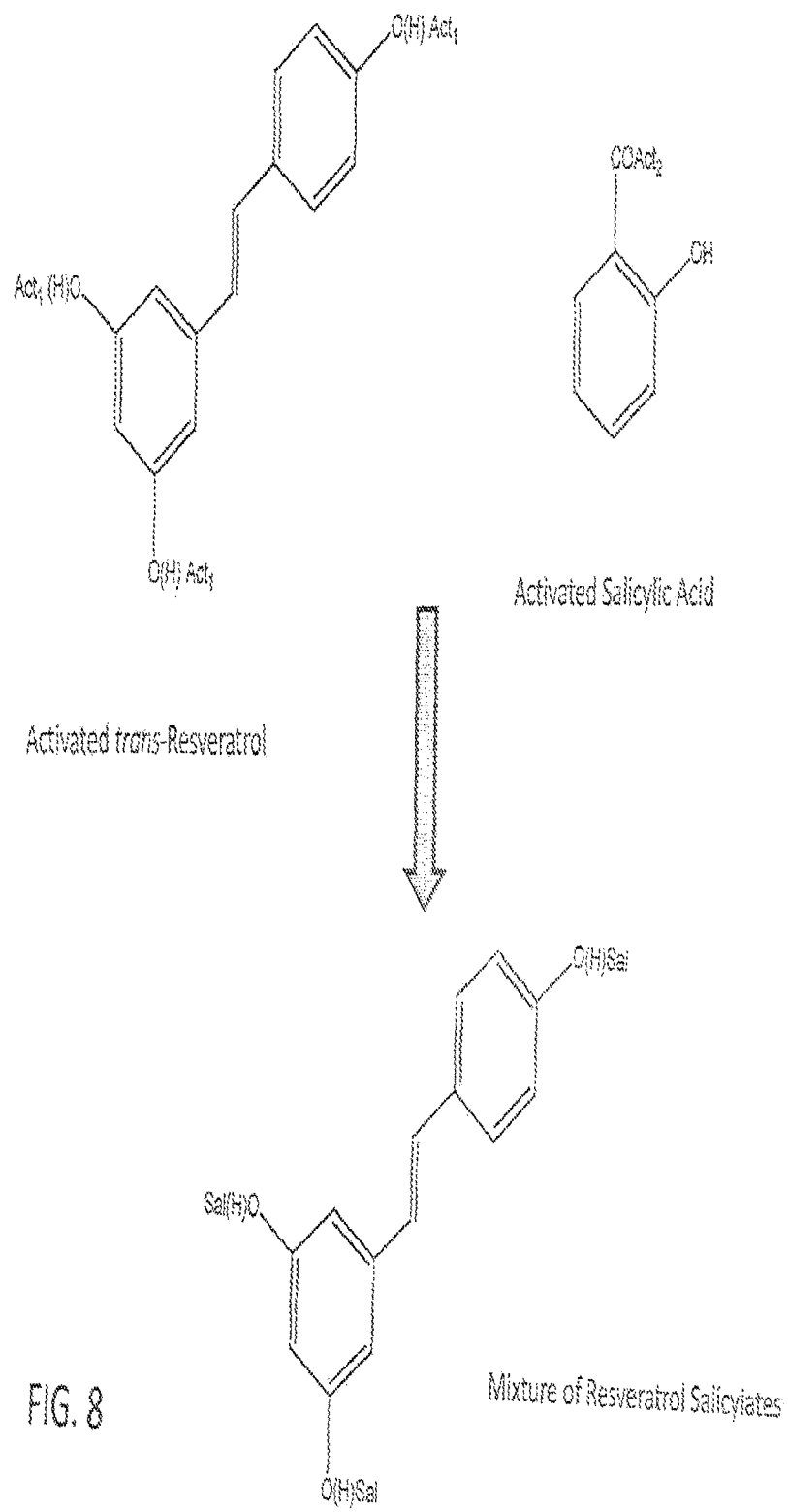
Figure 9:
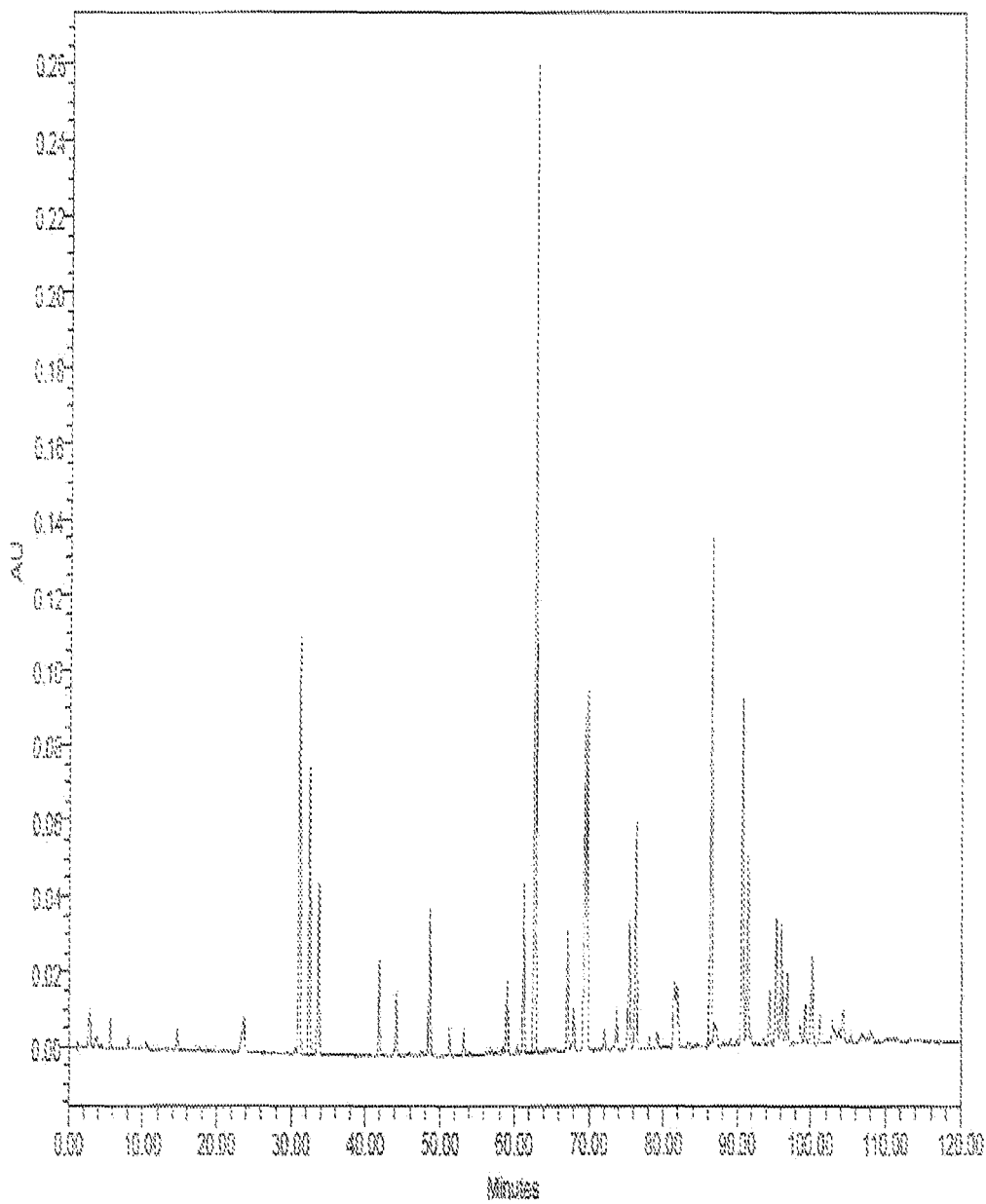
FIG. 9 shows chromatography data of a crude reaction mixture according to various embodiments herein.
Figure 12:
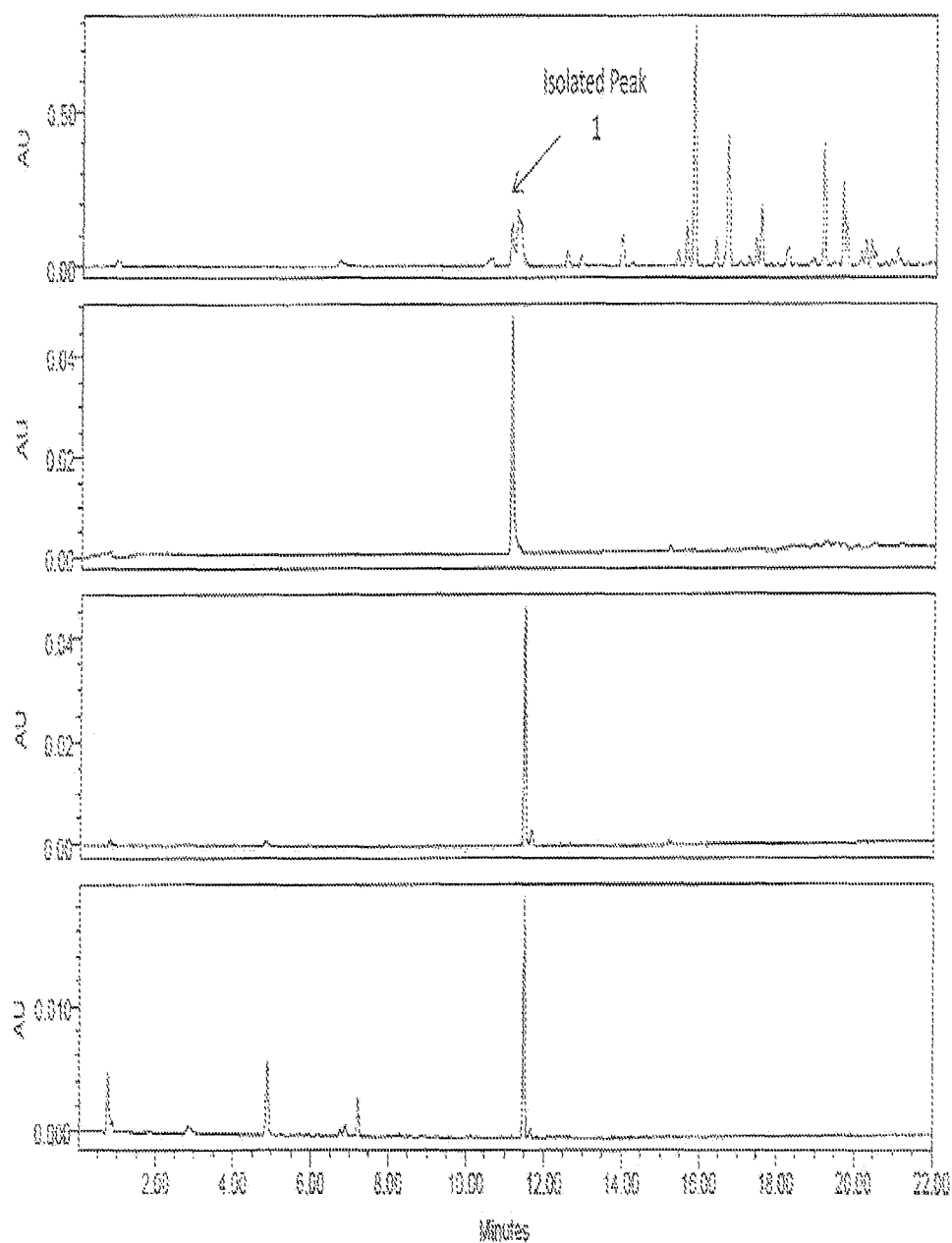
FIG. 12 shows chromatography data of a mixture according to various embodiments herein.
Figure 13:
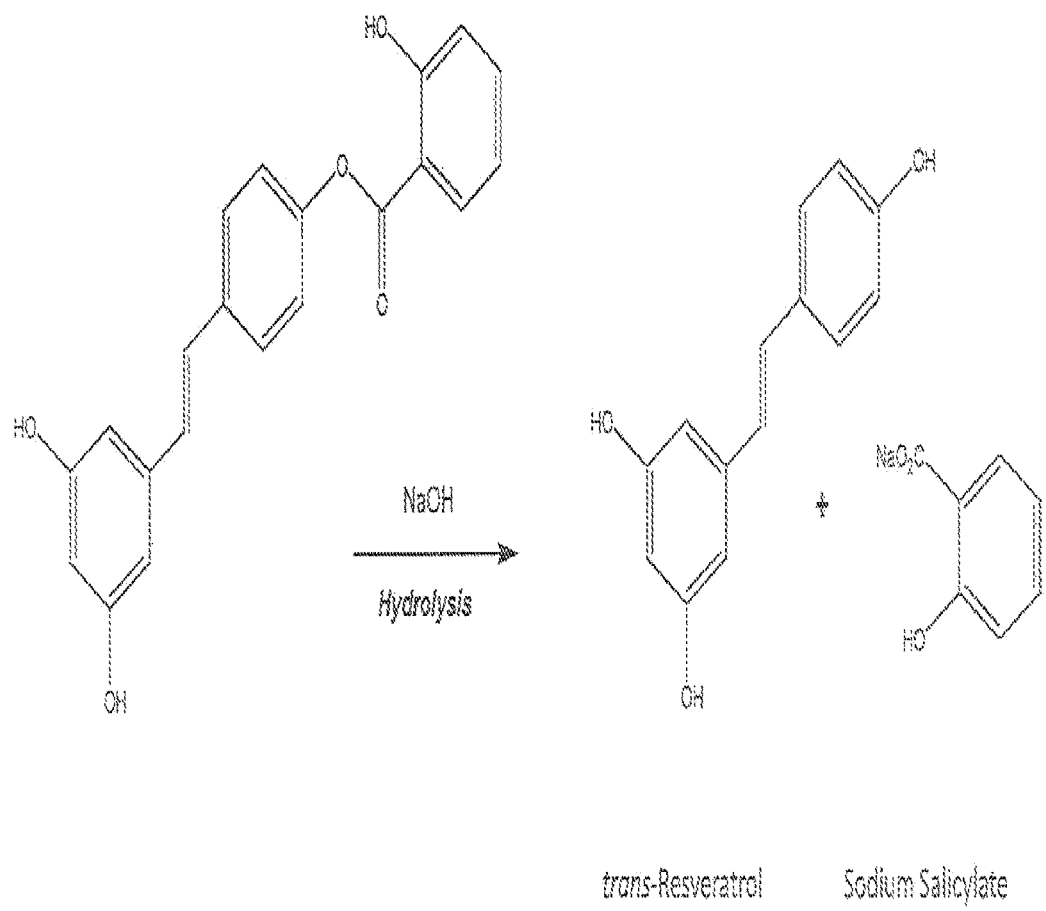
FIG. 13 shows reaction steps relating to the synthesis of trans-resveratrol and sodium salicylate according to various embodiments herein.
Figure 14:
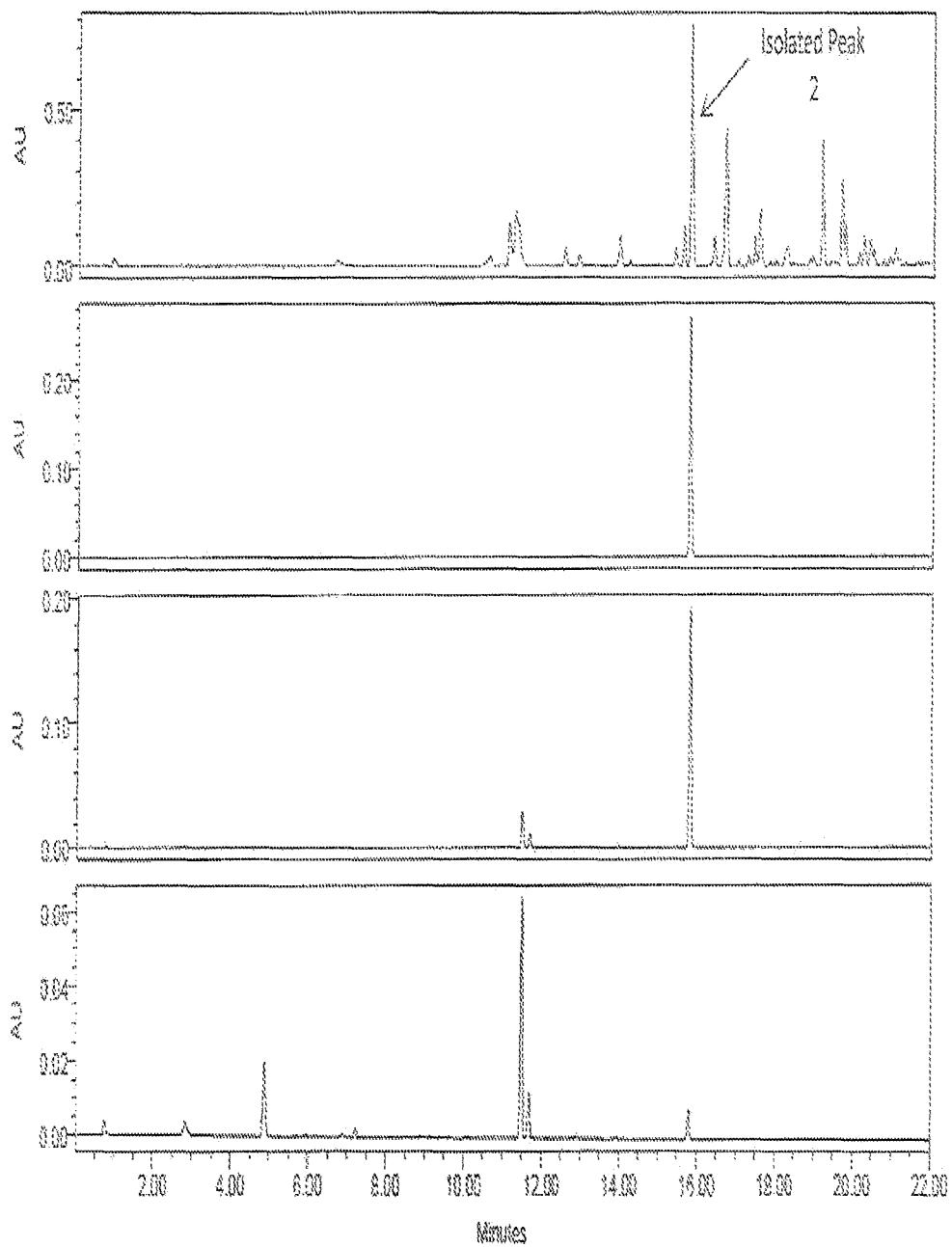
FIG. 14 shows chromatography data of a mixture according to various embodiments herein.
Figure 15:
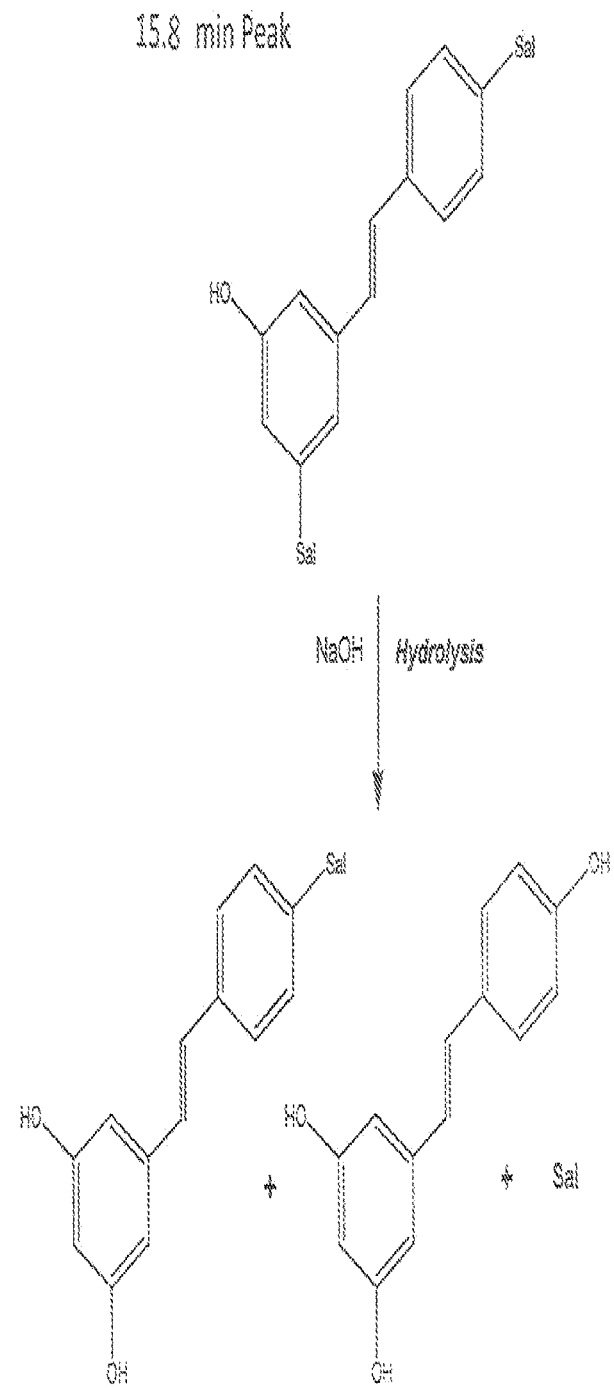
FIG. 15 shows reaction steps relating to a synthesis according to various embodiments herein.
Figure 16:
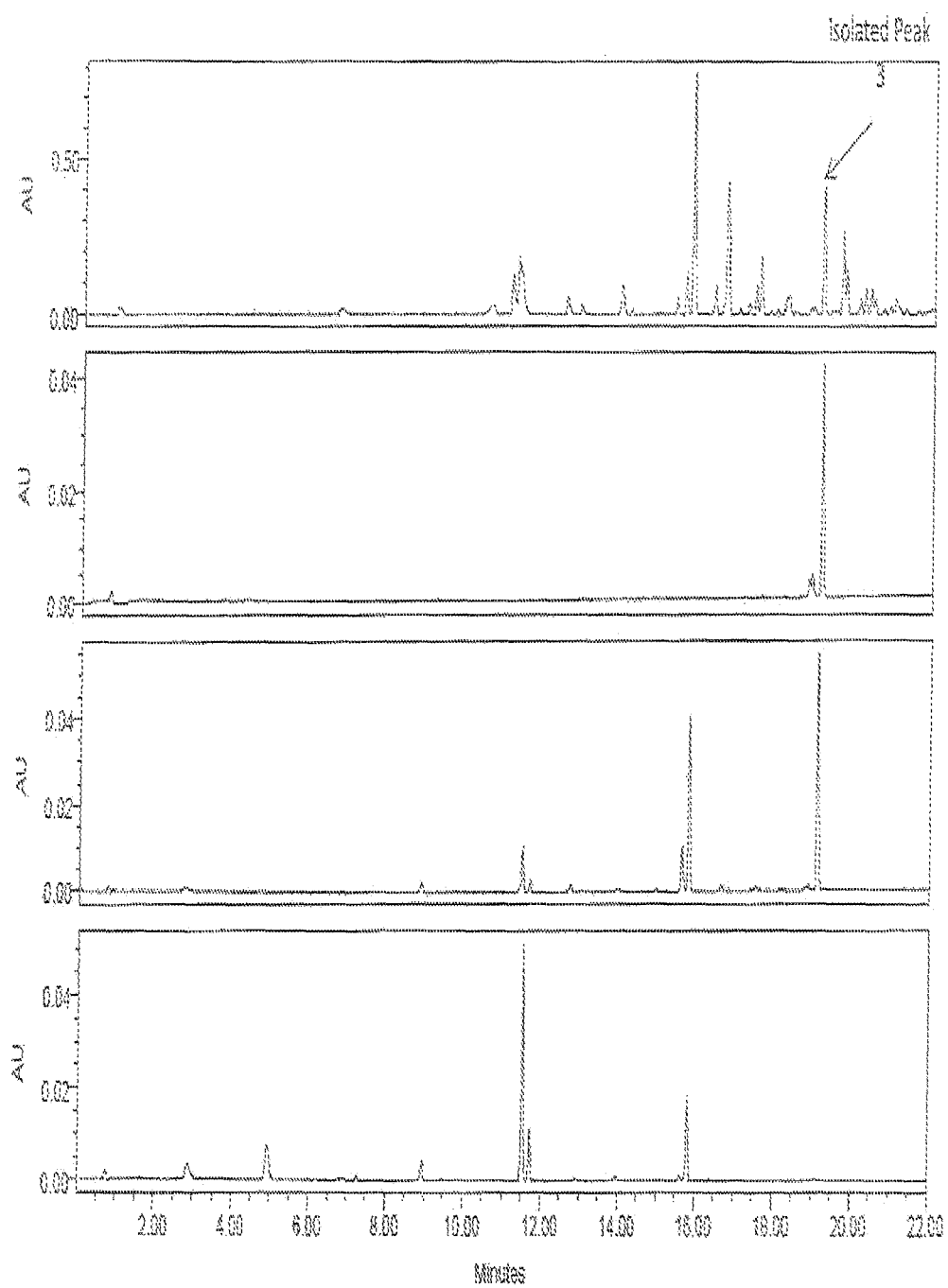
FIG. 16 shows chromatography data of a mixture according to various embodiments herein.
Figure 17:
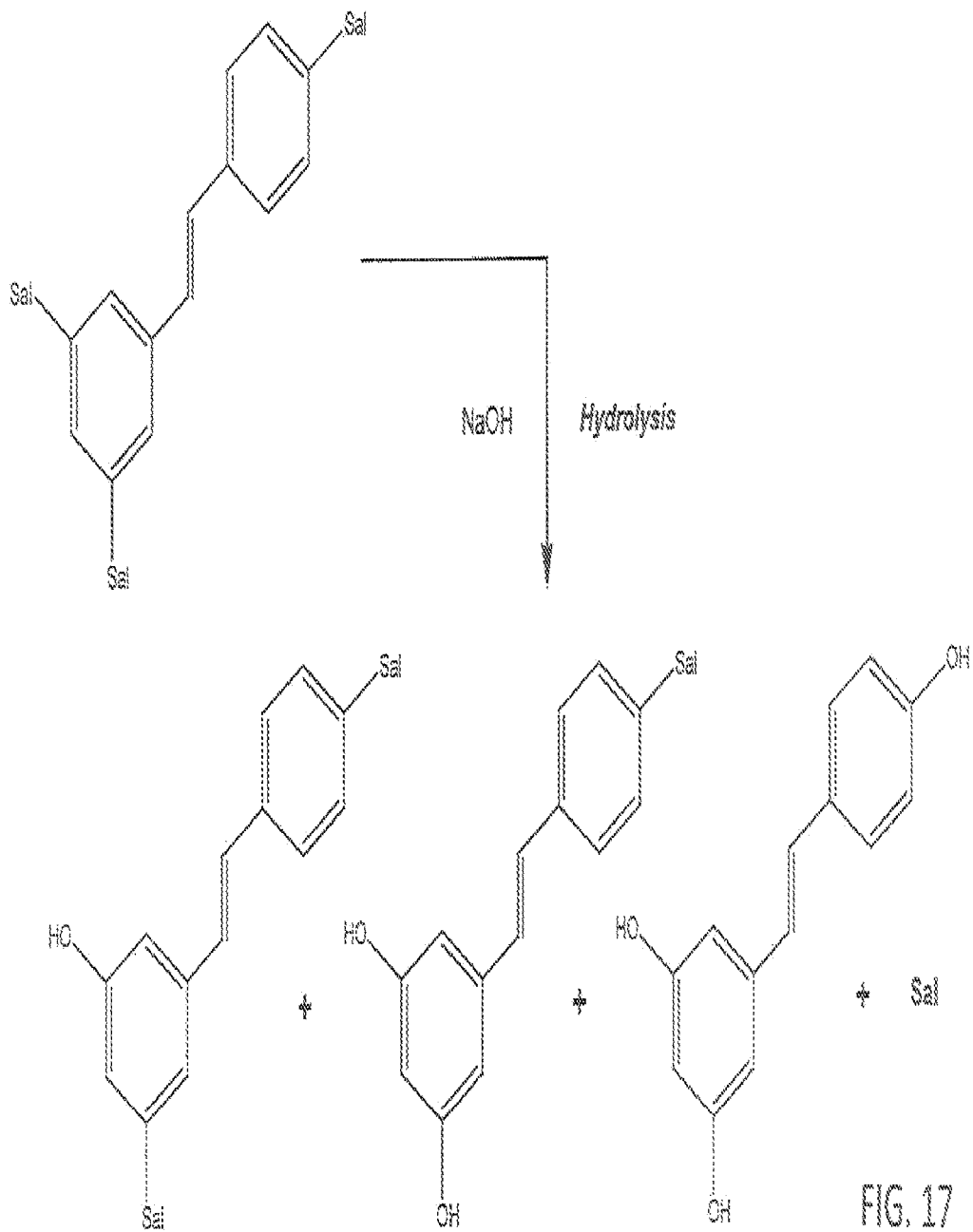
FIG. 17 shows reaction steps relating to a synthesis according to various embodiments herein.
Figure 18:
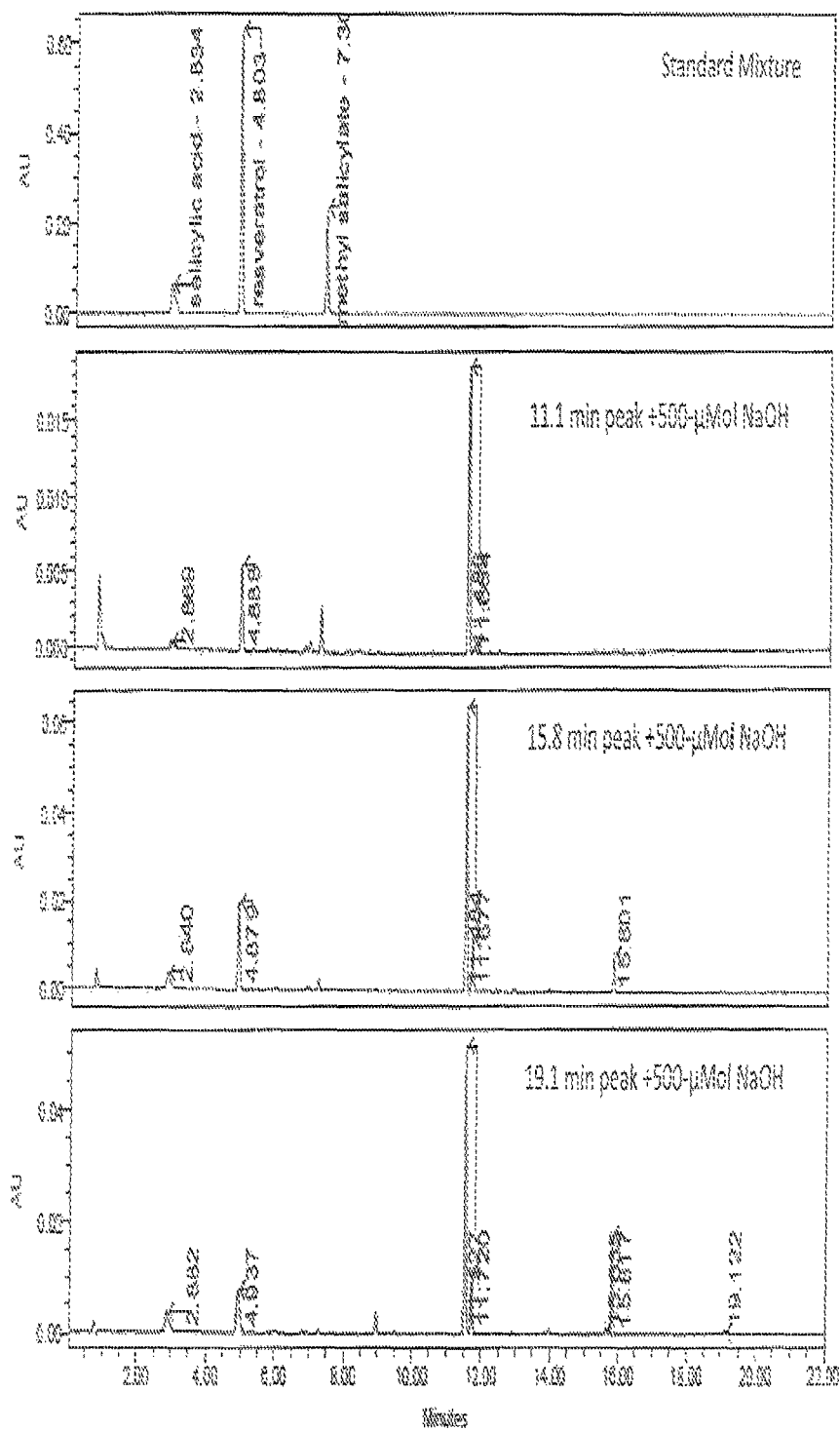
FIG. 18 shows chromatography data of mixtures according to various embodiments herein.

Advantages of this Example include the following: only one activator is required; the reaction can be performed in a single reactor and therefore dangers and time delays of transferring activated SA and resveratrol can be avoided; and there are significant cost savings associated with using only one reactor and only one activator. Certain embodiments in accordance with this Example are shown in FIGS. 4 through 6.

In certain embodiments, the present technology is directed to a method of synthesizing a mixture of mono-, di-, tri- or poly-substituted resveratrol salicylates, the method comprising the steps of: (a) combining activated salicylic acid with activated resveratrol in one or more solvents; and (b) controlling the ratio of substituted resveratrol salicylates by varying the molar ratio of activated salicylic acid to activated resveratrol. Certain embodiments of the present technology would also contemplate the step of controlling the hydrolysis of the poly-substituted resveratrol to yield a desired distribution of mono-, di-, tri- and poly-salicylate-modified resveratrol.

In the examples herein, the differently substituted compounds could be separated in a predictable manner. Both reaction work-up procedures and sophisticated HPLC-based purification and isolation protocols were developed, which allowed for separation and isolation of specifically substituted resveratrol salicylates. Thus, reliable chemistry for synthesizing salicylates according to the present technology has been developed. Chromatographic methods for reaction analysis and product isolation have been established. The composition and identity of the reaction products was established by limited and exhaustive hydrolysis and corroborated by mass spectroscopy, as shown, e.g., in FIGS. 7 through 24.

Figure 21:
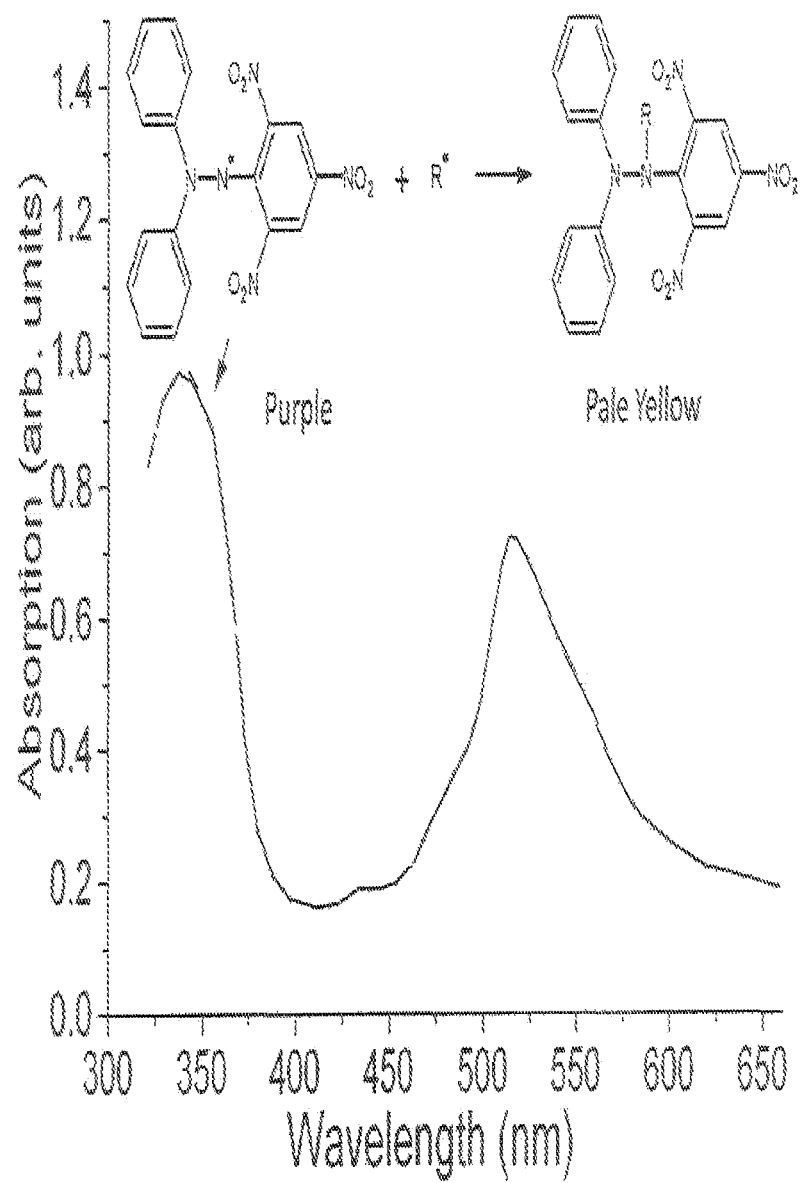
FIGS. 21-26 show data results from assays determining antioxidant activity of various mixtures and reaction products according to the technology herein.
Figure 22:
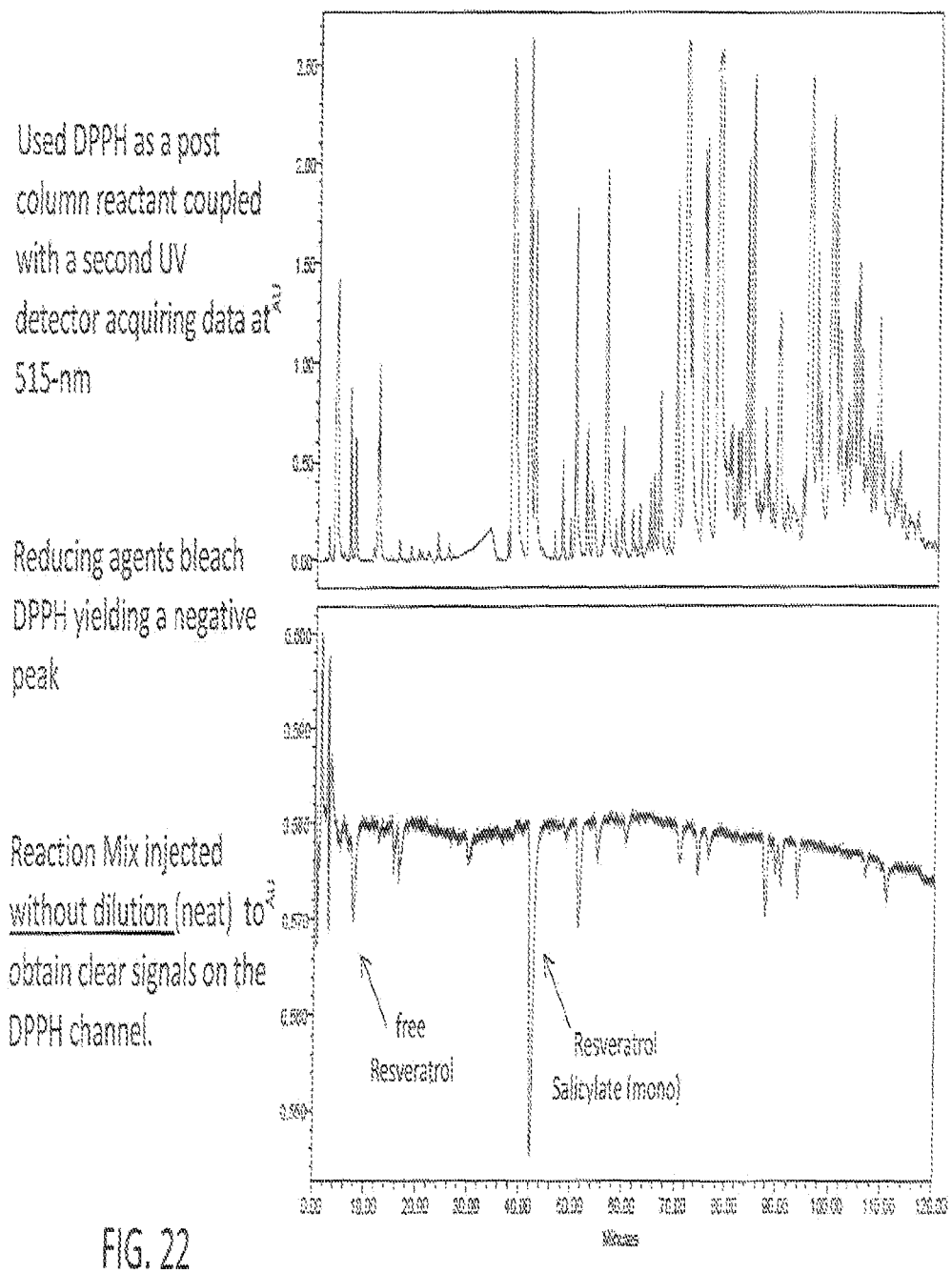
Figure 23:
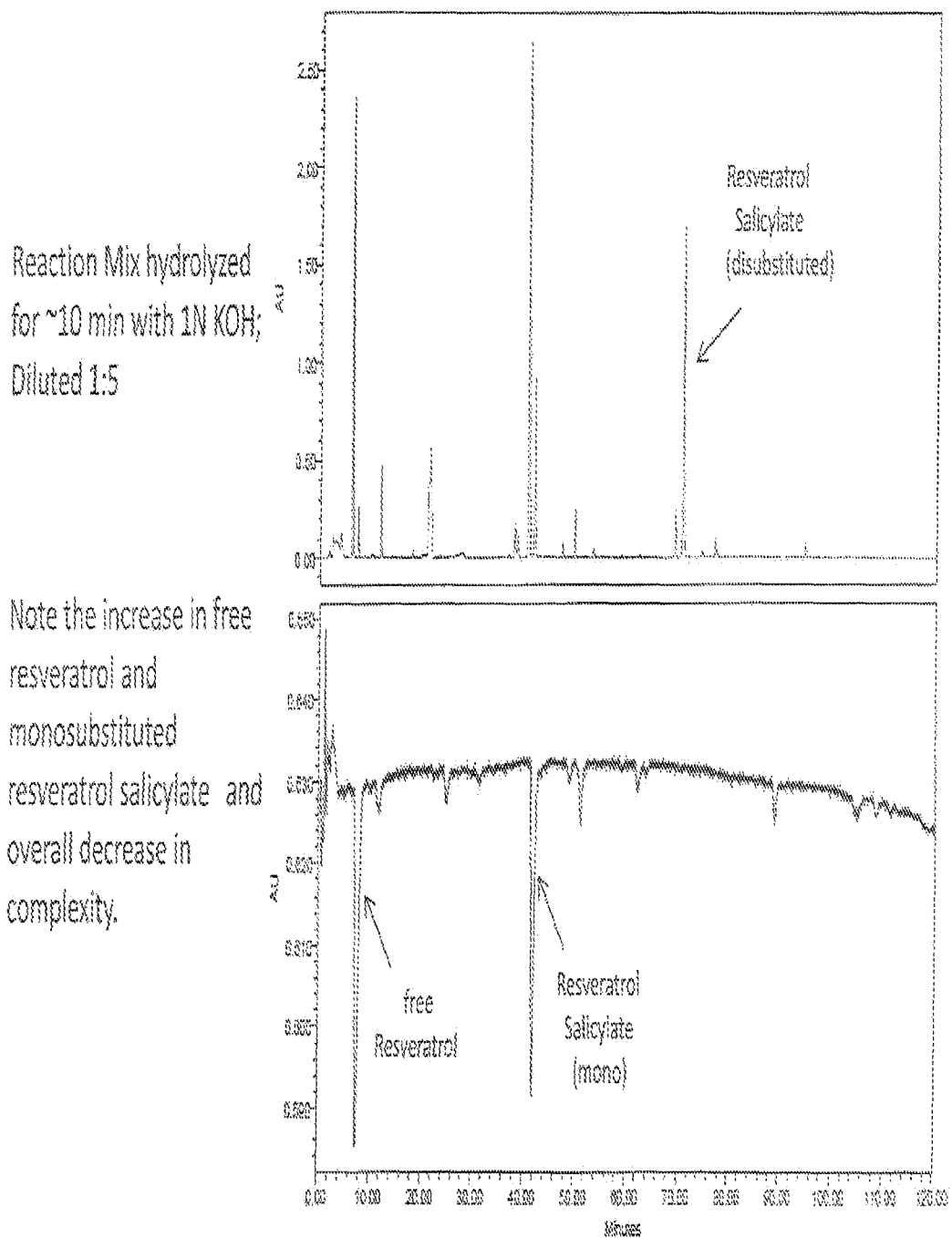
Figure 24:
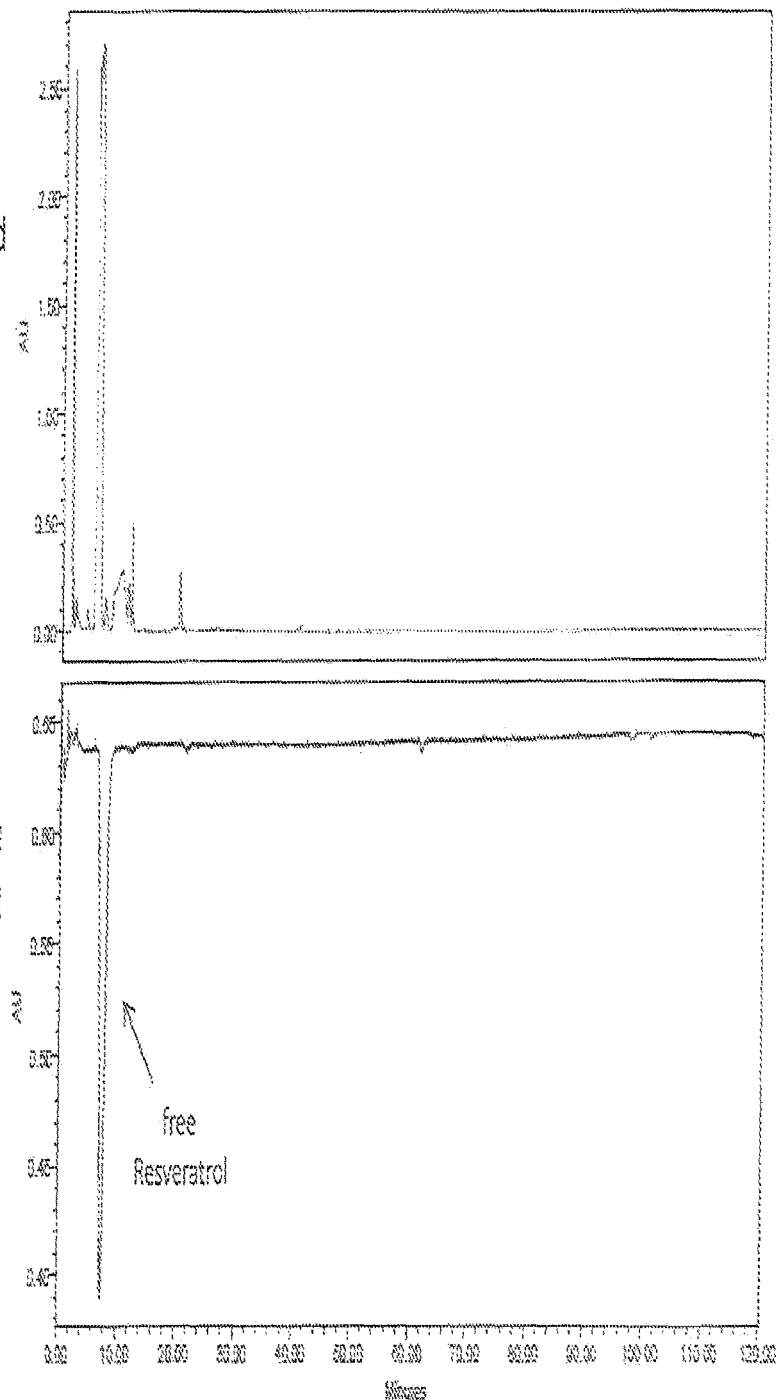

In particular, FIG. 21 shows results of absorption versus wavelength with a DPPH assay, indicating that the compositions herein exhibit high levels of antioxidant activity. Further, FIGS. 22-24 illustrate, among other things, an increase in free resveratrol and monosubstituted resveratrol salicylate, overall decrease in complexity and apparent loss of all other ester derivatives. In certain embodiments, reaction conditions can be optimized to generate desired product distributions, and evaluation of the antioxidant properties of resveratrol salicylates can be carried out by the HPLC DPPH assay.

Example 4

The cytotoxicity of compositions herein was measured. Human epidermal keratinocytes or dermal fibroblasts were seeded into 96-well plates and grown to confluence. Replicate wells were fed a medium containing varying concentrations of resveratrol salicylate mixture that was solubilized in DMSO. DMSO concentration was held constant (0.5%) in all wells including control wells that included zero resveratrol salicylate.

Figure 25:
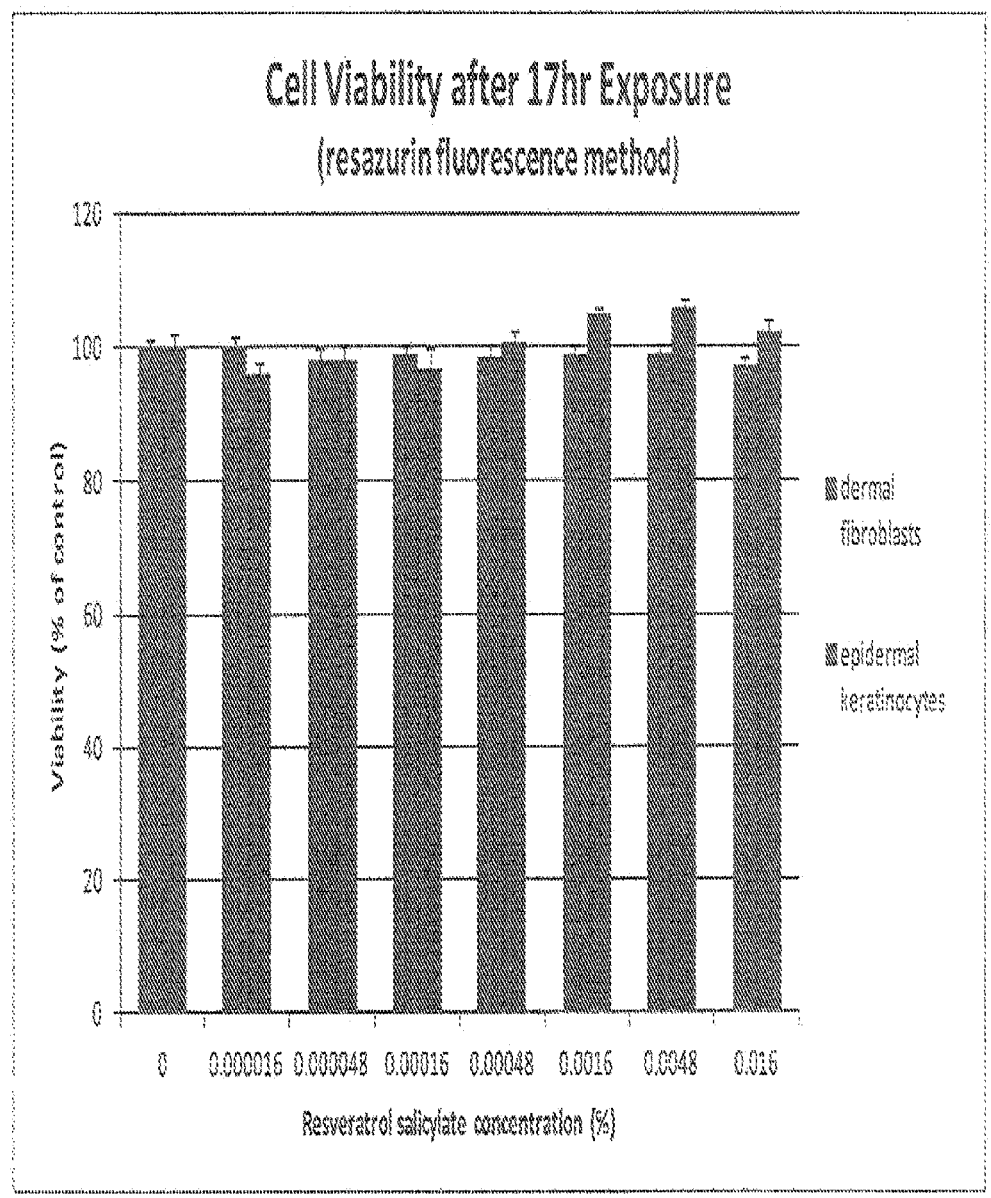
Figure 26:
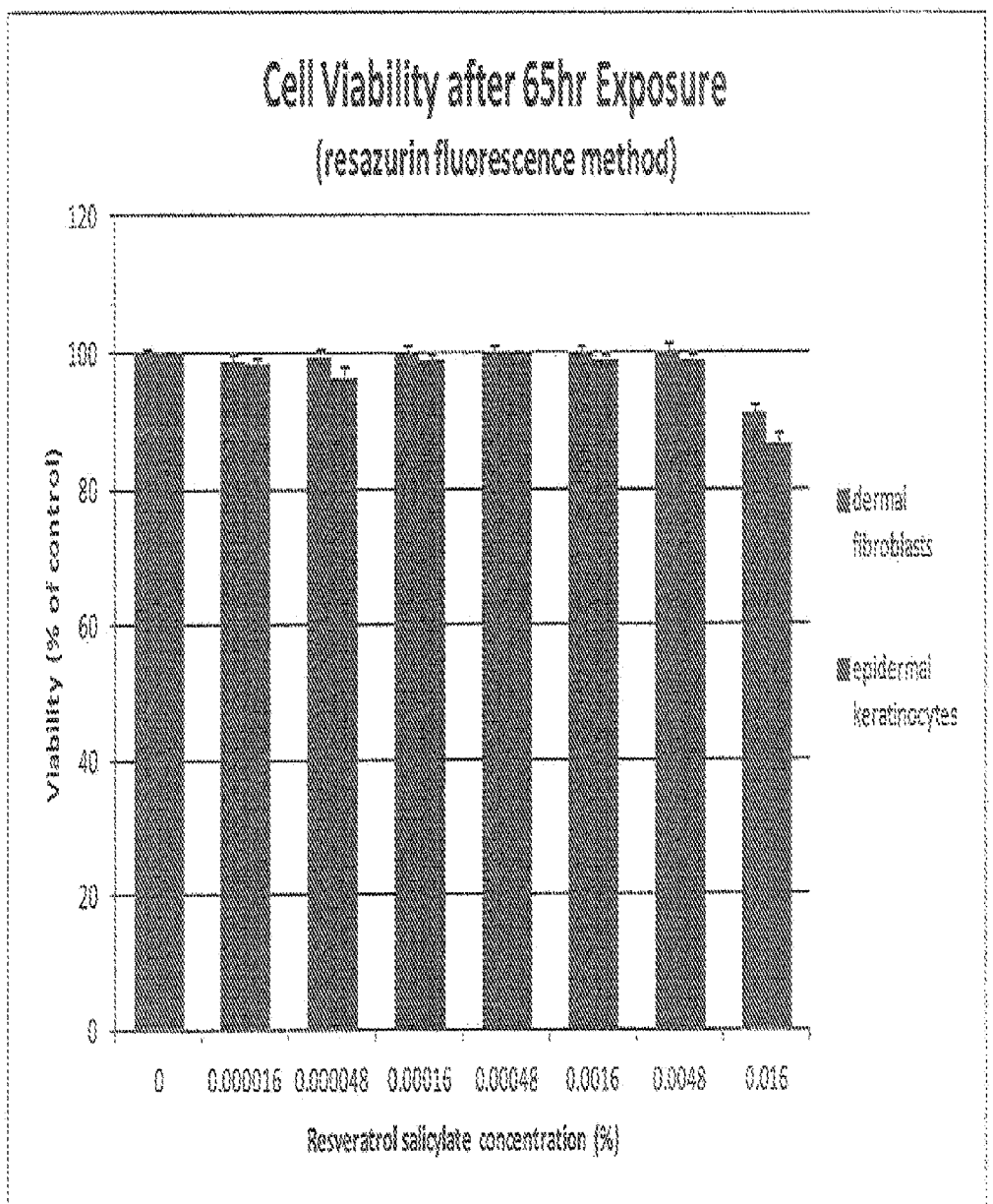

After contact with the resveratrol salicylate for either 17 or 65 hours, the media were removed and the cells incubated for 1 hour in buffered salt solution containing 42 μm resazurin. Fluorescence (ex530/em580) of resorufin (reduction product of resazurin) was measured after 1 hour. All data were normalized to the fluorescence of the control wells, representing 100% viability. The extent of resazurin reduction is a measure of total mitochondrial metabolic activity, and is proportional to cell number. Results are shown graphically in FIGS. 25 and 26, and show that resveratrol salicylate was only slightly toxic to both fibroblasts and keratinocytes at the highest tested concentration of 0.016%. This caused a decrease in viability of about 10% after the 65 hour exposure. However, the concentration was non-toxic after 17 hour exposure. All lower concentrations were non-toxic at both time points. As used herein, "non-toxic" means exhibiting cytotoxicity of less than about 5%. In certain embodiments, the resultant resveratrol salicylate mixture, when contacted with fibroblasts or keratinocytes, results in cytotoxicity of less than about 10% after 17 hours of contact. In certain embodiments, the mixtures herein have the further characteristic of resulting in cytotoxicity of less than about 20%, less than about 10% or less than about 5% after 65 hours of contact with fibroblasts or keratinocytes.

Figure 19:
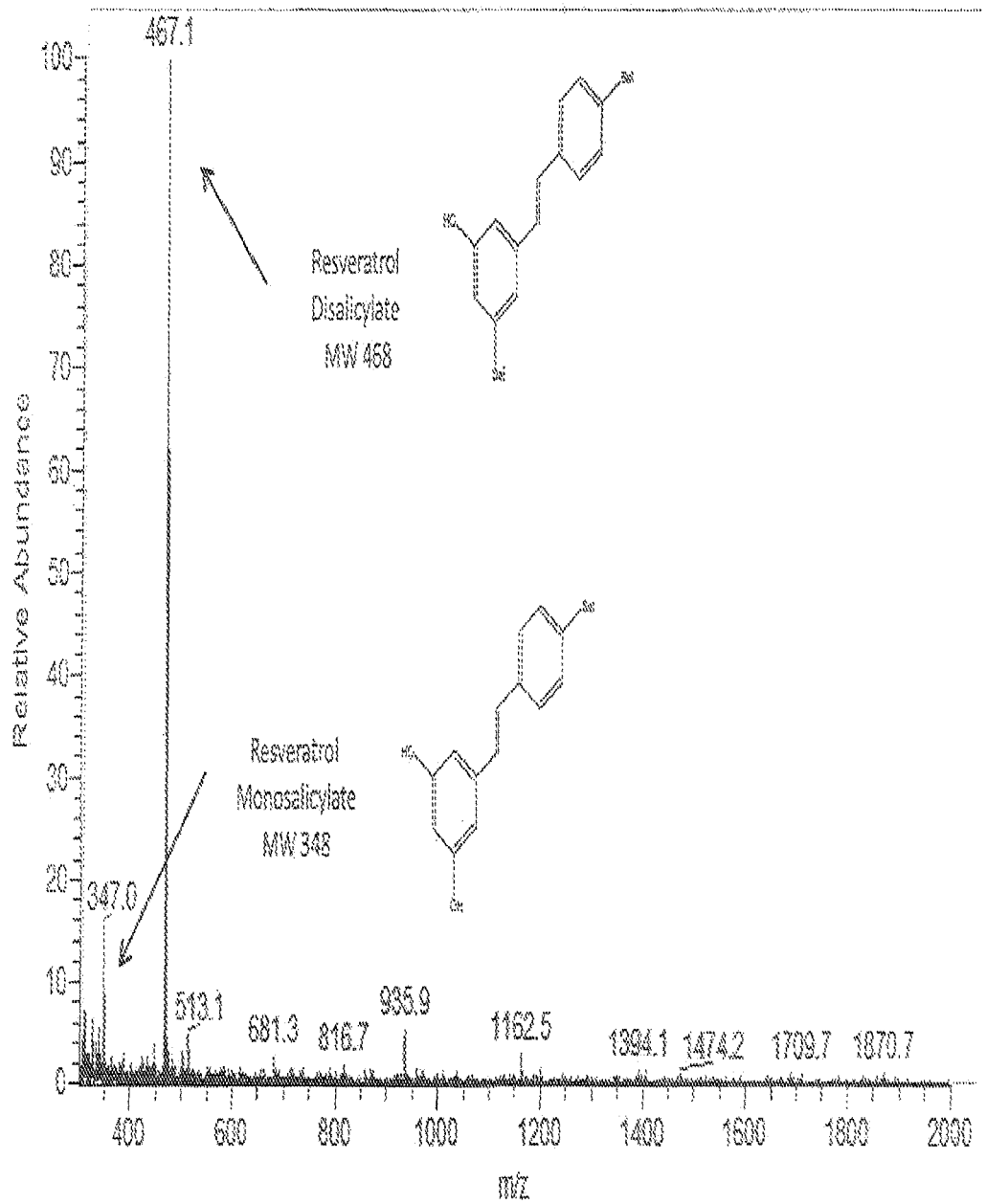
FIG. 19 shows mass spectroscopy analysis of a mixture according to various embodiments herein.
Figure 20:
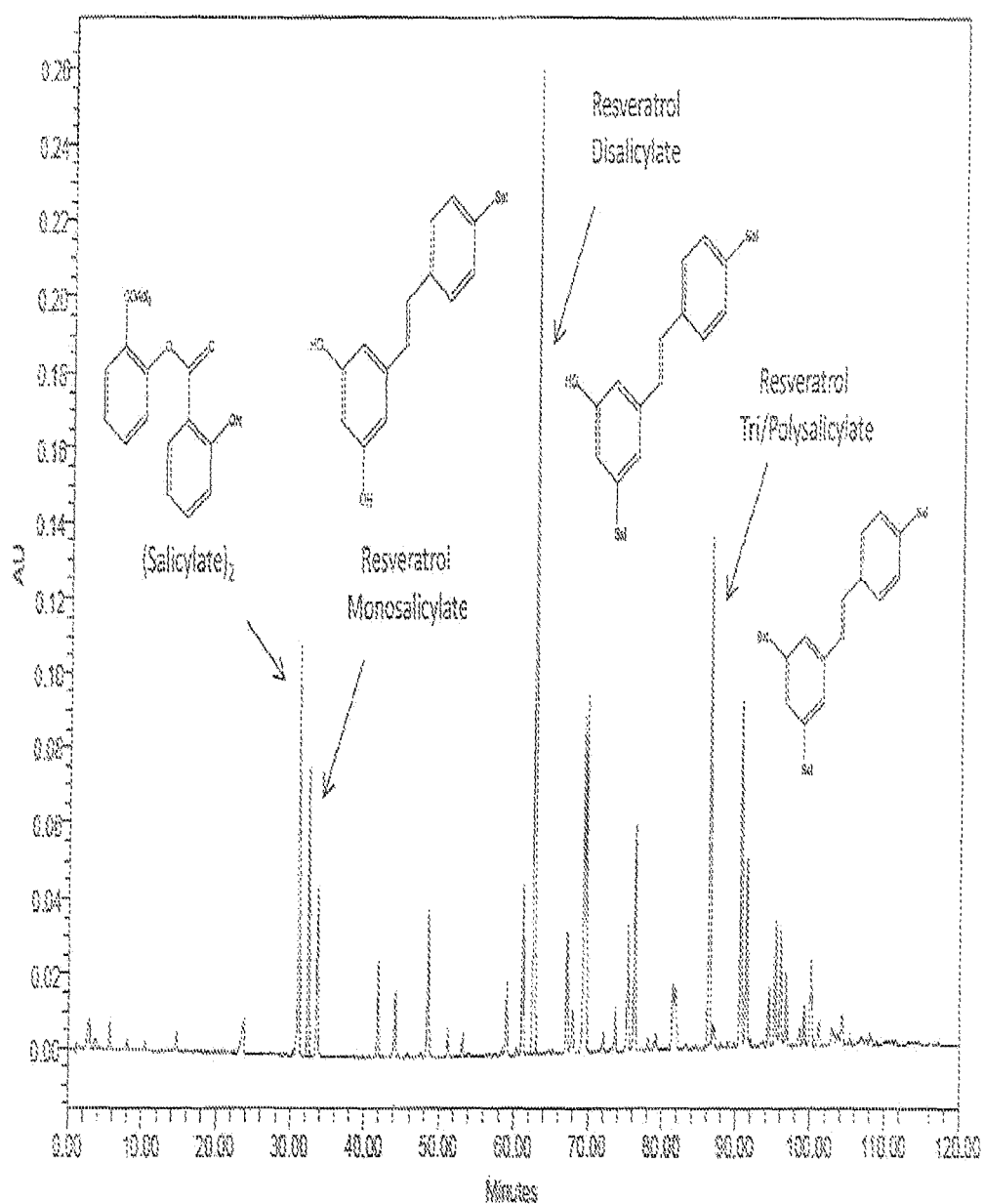
FIG. 20 shows chromatography data of a crude reaction mixture according to various embodiments herein.

FIGS. 6-8, 10, 11, 13, 15 and 17 show the synthesis of resveratrol derivatives as carried out according to certain embodiments herein. FIGS. 9, 12, 14, 16, 18 and 20 show analysis results of some exemplary mixtures that were created and tested, many of which show identifying peaks at various times. FIG. 19 shows a mass spectroscopy analysis, with a main product peak at 15.8 minutes. As can be seen in the Figures, it has been established herein that methods exist for predicting and quantifying desired results, in terms of distribution of resveratrol salicylates by desired degrees of substitution, and that the methods result in stable and high-quality products that have many industrial and commercial applications.

In contrast to the present technology, the Maes publication (U.S. Patent Application Publication No. 2012/0288460) does not describe the actual resveratrol salicylates synthesis. It gives the synthetic procedure for making resveratrol triphosphates instead, as set forth in WO 2006/029484A1. The work teaches treatment of resveratrol in basic conditions with dibenzylphosphate in the presence of dimethylaminopyridine (DMAP). Although this process might be acceptable for making resveratrol triphosphate, it cannot be used for preparing resveratrol salicylates. An analogous approach was tried with methyl salicylate and yielded no product. Moreover, described method is impractical as it uses carbon tetrachloride as solvent. Carbon tetrachloride is one of the most potent hepatotoxins and inducers of liver cancer.

An alternative approach, mentioned in U.S. Pat. No. 6,572,882, involves synthesis of carboxylic acid esters of resveratrol by the Schotten-Baumann reaction. The procedure is based on treatment of resveratrol in basic conditions with commercially available carboxylic acid chlorides. Although possible for simple carboxylic acids, the method cannot be used for making salicylates, as salicylic acid chloride cannot be prepared due to the presence of the interfering ortho-hydroxyl group.

In summary, the present technology is highly superior for many reasons, including but not limited to the following: the methods here are different from those known in the art; the methods here generate resveratrol salicylates as products, and these products can be confirmed (presence and identity) by both spectral and chemical analysis; and the methods here can be used to obtain many different resveratrol salicylates, including but not limited to resveratrol polysalicylates. The synthetic approaches and subsequent purification methods used herein can avoid toxic and mutagenic solvents, and are highly amenable to scaleup.

Although the present technology has been described in relation to particular embodiments thereof, these embodiments and examples are merely exemplary and not intended to be limiting. It will be apparent to one of ordinary skill in the art that aspects of the technology, as described above, may have many applications. The present technology should, therefore, not be limited by the specific disclosure herein, and can be embodied in other forms not explicitly described here, without departing from the spirit thereof.

What is claimed:

1. A method of synthesizing a resveratrol salicylate, the method comprising the steps of:
   (a) contacting resveratrol and salicylic acid with a solvent to provide a solution comprising resveratrol and salicylic acid; and
   (b) contacting the solution with an activator under conditions that allow for formation of activated salicylic acid, which reacts with the resveratrol to form a resveratrol salicylate;
   wherein the activator is selected from the group consisting of
      (i) a carbodiimide selected from the group consisting of N,N'-Dicyclohexylcarbodiimide (DCC); N,N'-diisopropylcarbodiimide (DIC); N-Cyclohexyl-N'-(2-morpholinoethyl)carbodiimide methyl-p-toluenesulfonate (CMC); 1-tert-Butyl-3-ethylcarbodiimide; 1-Ethyl-3-(3-dimethylaminopropyl)carbodiimide (EDC); N,N'-Di-tert-butylcarbodiimide; N-(3-Dimethylaminopropyl)-N'-ethylcarbodiimide; and 1,3-Di-p-tolylcarbodiimide;
      (ii) a diimidazole selected from the group consisting of 1,1'-Carbonyldiimidazole; 1,1'-Thiocarbonyldiimidazole; and 1,1''-Oxalyldiimidazole; and
      (iii) a uronium or phosphonium reagent selected from the group consisting of O-(Benzotriazol-1-yl)-N,N,N',N'-tetramethyluronium tetrafluoroborate; (7-Azabenzotriazol-1-yloxy)tripyrrolidinophosphonium hexafluorophosphate; (Benzotriazol-1-yloxy)tris(dimethylamino)phosphonium hexafluorophosphate; N,N,N',N'-Tetramethyl-O—(N-succinimidyl)uronium tetrafluoroborate (TSTU); 1-[Bis(dimethylamino)methylene]-1H-1,2,3-triazolo[4,5-b]pyridinium 3-oxid hexafluorophosphate (HATU); N,N,N',N'-Tetramethyl-O-(1H-benzotriazol-1-yl)uronium hexafluorophosphate (HBTU); and (1-Cyano-2-ethoxy-2-oxoethylidenaminooxy)dimethylamino-morpholinocarbenium hexafluorophosphate (COMU).

2. The method of claim 1, further comprising the step of:
   (c) removing the solvent from the solution in (b) to provide a solid resveratrol salicylate.

3. The method of claim 1, wherein the solvent is at least one selected from the group consisting of acetonitrile; dimethylsulfoxide (DMSO); Hexamethylphosphoramide (HMPA); 1,3-Dimethyl-3,4,5,6-tetrahydro-2(1H)-pyrimidinone (DMPU); 1,3-Dimethyl-2-imidazolidinone (DMI); dimethylformamide (DMF); and 1-Methyl-2-pyrrolidinone (NMP).

4. The method of claim 1, wherein the carbodiimide in (i) is used in combination with N-hydroxysuccinimide (NHS) or dimethylaminopyridine (DMAP).

5. The method of claim 1, wherein step (b) is run at a temperature of about 10-85° C.

6. The method of claim 1, wherein the resveratrol salicylate, wherein contacted with fibroblasts or keratinocytes, results in cytotoxicity of less than about 10% after 17 hours of contact.

7. The method of claim 1, wherein the resveratrol salicylate, wherein contacted with fibroblasts or keratinocytes, results in cytotoxicity of less than about 20% after 65 hours of contact.

8. The method of claim 1, wherein the resveratrol salicylate comprises at least one compound selected from the group consisting of a resveratrol mono-salicylate, a resveratrol di-salicylate, and a resveratrol tri-salicylate.

9. The method of claim 1, further comprising the step of partially hydrolyzing the resveratrol salicylate.

* * * * *